United States Patent
Itoh

(10) Patent No.: US 7,314,596 B2
(45) Date of Patent: Jan. 1, 2008

(54) APPARATUS FOR SENSING COAGULATION OF BLOOD SAMPLE

(75) Inventor: Teruaki Itoh, Kumamoto (JP)

(73) Assignee: IDS Company, Ltd., Kumamoto (JP)

( * ) Notice: Subject to any disclaimer, the term of this patent is extended or adjusted under 35 U.S.C. 154(b) by 382 days.

(21) Appl. No.: 11/056,123

(22) Filed: Feb. 14, 2005

(65) Prior Publication Data

US 2005/0180884 A1    Aug. 18, 2005

(30) Foreign Application Priority Data

Feb. 16, 2004    (JP)    ............... 2004-038085

(51) Int. Cl.
*G01N 33/86* (2006.01)
*G01N 35/02* (2006.01)
*G01N 21/00* (2006.01)

(52) U.S. Cl. ............... 422/73; 422/63; 422/64; 422/65; 422/82.05; 436/43; 436/47; 436/48; 436/63; 436/69; 436/164; 436/165; 600/369; 73/64.41; 73/64.43

(58) Field of Classification Search ............... 436/43, 436/45, 47, 48, 63, 69, 164, 165, 174; 422/63, 422/64, 65, 67, 68.1, 73, 82.05, 82.09; 600/369; 73/64.41, 64.43
See application file for complete search history.

(56) References Cited

U.S. PATENT DOCUMENTS

| | | | | |
|---|---|---|---|---|
| 3,754,866 A | * | 8/1973 | Ritchie et al. | 422/73 |
| 4,105,411 A | * | 8/1978 | Biver | 422/73 |
| 4,120,662 A | * | 10/1978 | Fosslien | 73/864.24 |
| 4,278,437 A | * | 7/1981 | Haggar | 436/165 |
| 4,609,017 A | * | 9/1986 | Coulter et al. | 141/1 |
| 5,283,178 A | * | 2/1994 | Kessler et al. | 435/7.25 |

FOREIGN PATENT DOCUMENTS

NL    6807521    * 12/1969

* cited by examiner

*Primary Examiner*—Maureen M. Wallenhorst
(74) *Attorney, Agent, or Firm*—Nixon & Vanderhye P.C.

(57) ABSTRACT

A blood sample sensing apparatus includes a moving device which moves a sample container containing a blood sample to a sensing position, a turning mechanism which is connected to the moving device and tilts the sample container such that a bottom of the sample container is directed upward when the sample container is located in the sensing position, and an optical sensor which is located in the sensing position and determines whether the blood sample in the sample container is coagulated.

12 Claims, 3 Drawing Sheets

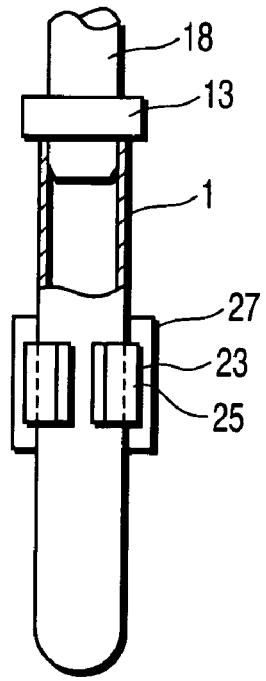
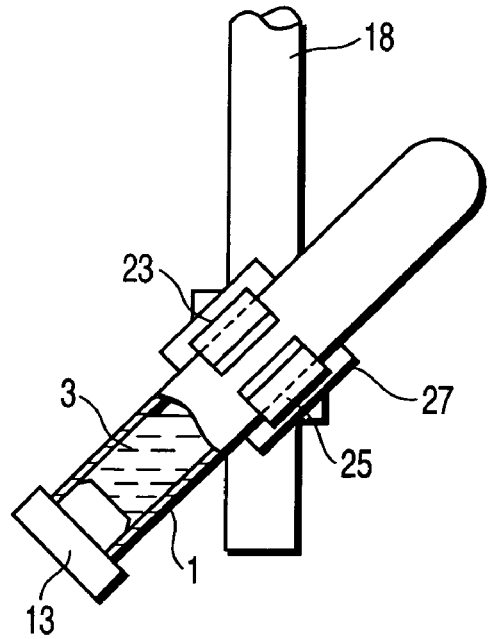
FIG. 3A                FIG. 3B
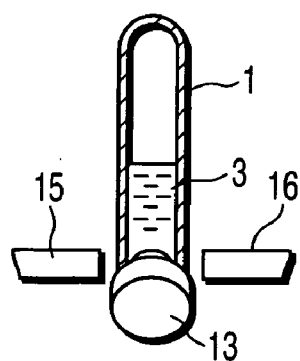
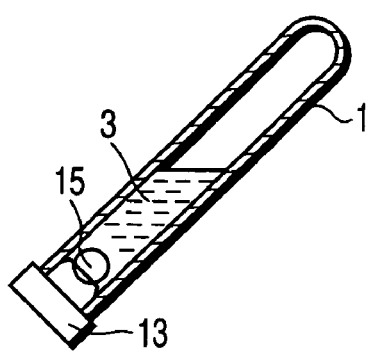
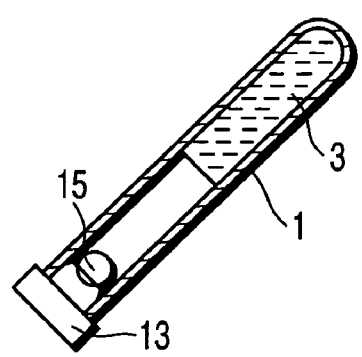
FIG. 4A        FIG. 4B        FIG. 4C

APPARATUS FOR SENSING COAGULATION OF BLOOD SAMPLE

CROSS-REFERENCE TO RELATED APPLICATIONS

This application is based upon and claims the benefit of priority from prior Japanese Patent Application No. 2004-038085, filed Feb. 16, 2004, the entire contents of which are incorporated herein by reference.

BACKGROUND OF THE INVENTION

1. Field of the Invention

The present invention relates to an apparatus for automatically sensing whether a blood sample collected in a sample container is coagulated.

2. Description of the Related Art

When various blood tests such as biochemical analysis are conducted, a collected blood sample is contained and held in a sample container such as a test tube until it is tested. As the preprocessing of the blood tests, the blood sample is centrifuged to aliquot serum in the test tube. The serum is dispensed to a test container or the like.

If, however, the collected blood sample is left as it is for about half a day to all day, it will be coagulated in the test tube. The test tube is held and stored in a test tube holder or a test tube rack. The blood sample is therefore accumulated and coagulated at the bottom of the test tube.

If the blood sample is coagulated in the test tube, the coagulation will adversely affect the test. An operator therefore has to confirm whether the blood sample is coagulated or not before the test. However, even though the operator visually checks the test tube held vertically in the test tube holder or the test tube rack, he or she cannot confirm whether the blood sample is coagulated.

The operator therefore removes a number of test tubes from the test tube holder or the test tube rack one by one and visually checks whether the blood sample is fluid while tilting and shaking it to thereby determine whether the blood sample is coagulated.

However, the above operation becomes an enormous burden on the operator.

BRIEF SUMMARY OF THE INVENTION

In accordance with one embodiment of the present invention, there is provided a blood sample sensing apparatus capable of automatically taking out a sample container containing a blood sample and sensing whether the blood sample is coagulated in the sample container with high efficiency and high reliability.

The blood sample sensing apparatus comprises a sample container which contains a blood sample, a moving unit which moves the sample container to a sensing position, a turning mechanism which tilts the sample container such that an upper portion of the sample container is directed downward while a lower portion thereof is directed upward when the sample container is located in the sensing position, and an optical sensor which senses the blood sample accumulated in the upper portion of the sample container that is tilted by the turning mechanism.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a front view of a blood sample that has not been tilted by a holding hand turning mechanism of the apparatus according to the embodiment of the present invention;

FIG. 3B is a front view of the blood sample that has been tilted by the holding hand turning mechanism of the apparatus according to the embodiment of the present invention;

FIG. 4A is a side view of the blood sample that is sensed as not being coagulated by an optical sensing unit of the apparatus according to the embodiment of the present invention;

FIG. 4B is a front view of the blood sample that is sensed as not being coagulated by the optical sensing unit of the apparatus according to the embodiment of the present invention; and FIG. 4C is a front view of the blood sample that is sensed as being coagulated by the optical sensing unit of the apparatus according to the embodiment of the present invention.

DETAILED DESCRIPTION OF THE INVENTION

An embodiment of the present invention will be described with reference to the accompanying drawings.

(Configuration of Blood Sample Sensing Apparatus)

Figure 1:
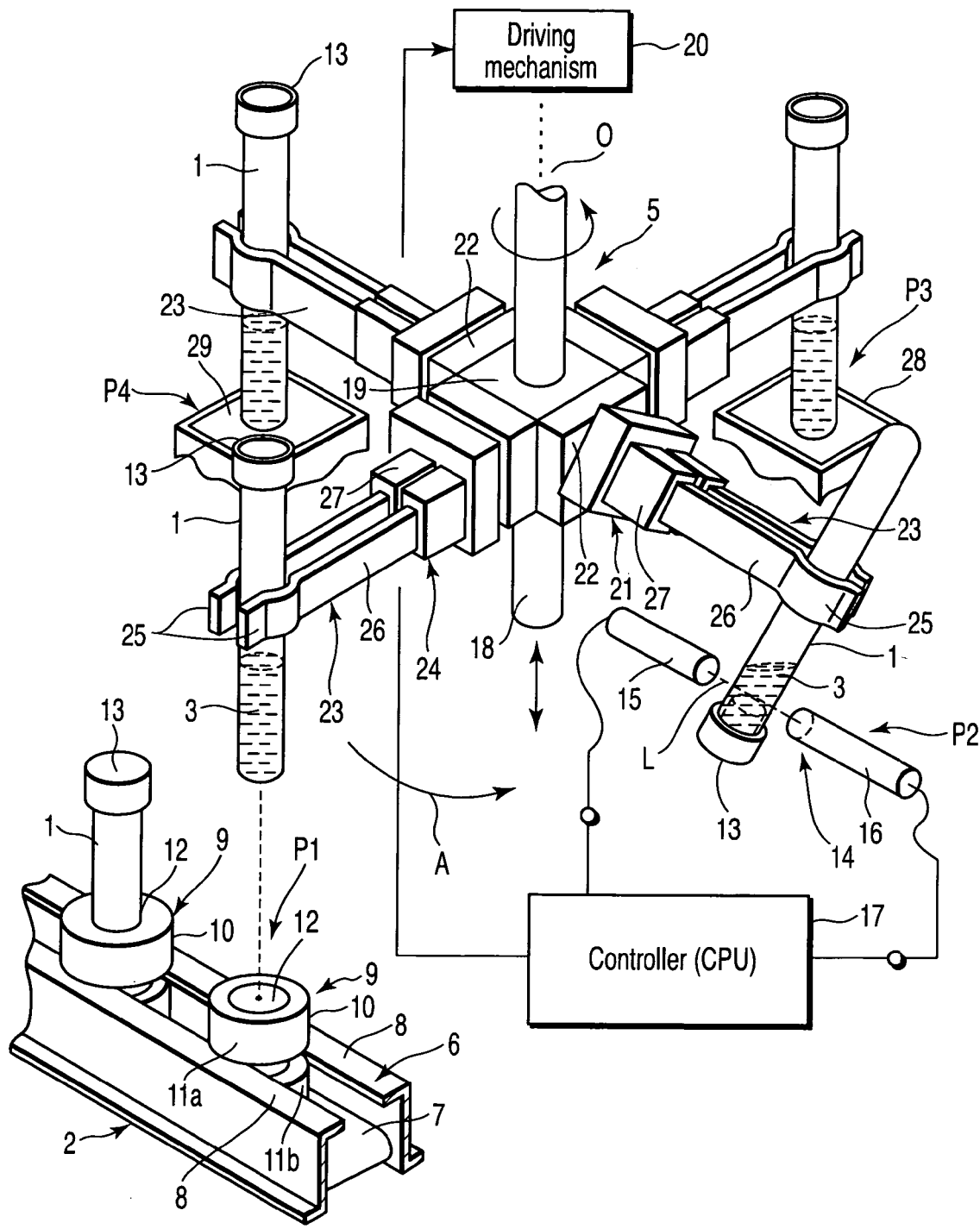
FIG. 1 is a perspective view of the configuration of the entire apparatus for sensing coagulation of a blood sample according to an embodiment of the present invention.
Figure 2A:
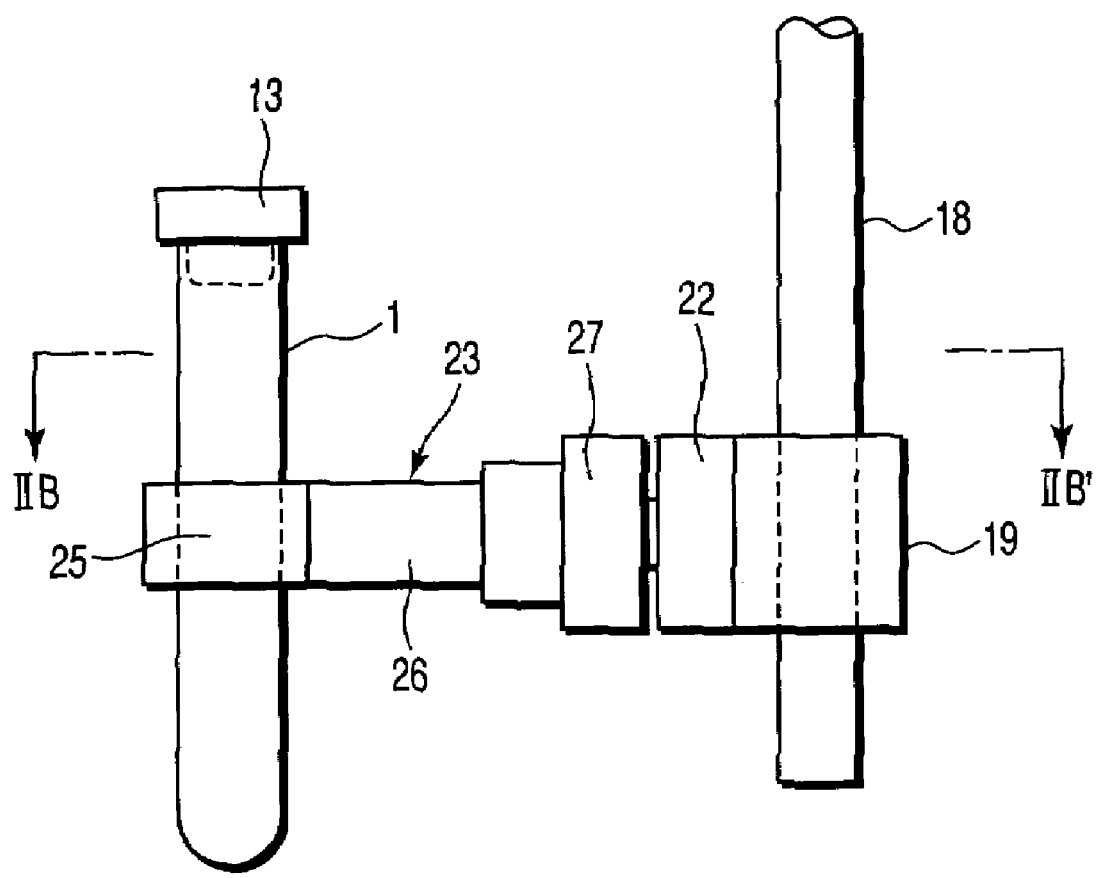
FIG. 2A is a side view of a holding hand of the apparatus according to the embodiment of the present invention.
Figure 2B:
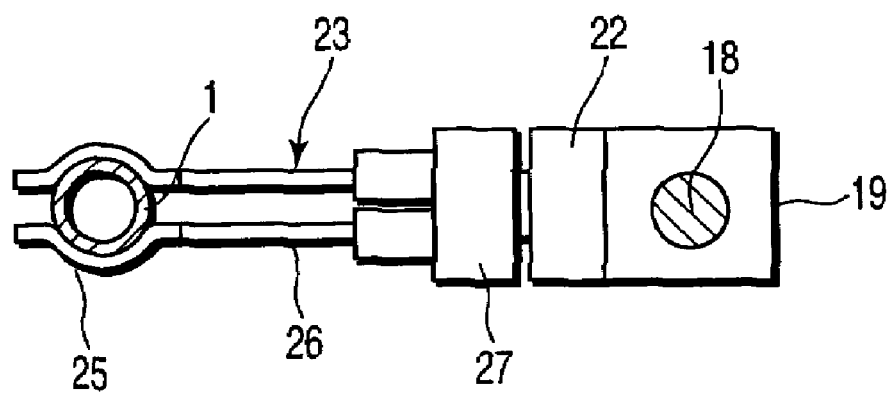
FIG. 2B is a sectional view taken along line IIB-IIB' shown in FIG. 2A.

FIG. 1 illustrates an apparatus for sensing coagulation of a blood sample. In this apparatus, a transfer position P1, a sensing position P2, a first separation position P3 and a second separation position P4 are set at 90-degree intervals around axis 0.

A conveyance path 2 for conveying a sample container 1 such as a test tube is provided in the transfer position P1. The conveyance path 2 includes gutter-shaped guide rails 6 that are made of metal such as aluminum and a conveyor belt 7 that runs endlessly in its longitudinal direction along the inner bottoms of the guide rails 6. The guide rails 6 are opposed to each other, and each has a folded edge 8 that protrudes in which direction an upper opening formed by the guide rails 6 is narrowed.

A number of sample container holders 9 each for vertically supporting the sample container 1 are slidably held in the guide rails 6. The sample container holders 9 are moldings made of synthetic resin. The sample container holders 9 each include a cylindrical holder main body 10, and the holder main body 10 has a pair of collars 11a and 11b in the vertical direction. The folded edges 8 are vertically sandwiched and held between the collars 11a and 11b. The holder main body 10 has a holding hole 12 at its top. The lower end portion of the sample container 1 is detachably inserted into the holding hole 12. The holder main body 10 is brought into contact with the top surface of the conveyor belt 7 at its bottom and conveyed by friction therebetween.

The sample container 1 is made of transparent glass, and its top opening is closed with a cap 13 made of rubber, synthetic resin or the like. Thus, even though the sample container 1 is tilted or reversed, a blood sample 3 does not overflow from the container 1.

An optical sensing unit 14 is provided in the sensing position P2 to optically sense coagulation of the blood sample 3 in the sample container 1. The sensing unit 14 includes a light-emitting element 15 and a light-receiving element 16, which are opposed to and separated from each other. These elements 15 and 16 are connected to a controller 17. When test light L emitted from the light-emitting element 15 passes through the top portion of the sample container 1 which is directed downward, the sensing unit 14 determines that the blood sample 3 is coagulated at the bottom of the container which is directed upward. When the test light L is shielded by the blood sample 3, the sensing unit 14 determines that the blood sample 3 is not coagulated.

A rotor 5 is provided as a driver on the axis 0. The rotor 5 extends in the vertical direction and has a main shaft 18 that can be freely rotated and moved up and down. A rectangular block 19 is provided at a midway point of the main shaft 18. The main shaft 18 is moved up and down and rotated intermittently by means of a driving mechanism 20 that is controlled by the controller 17. A rotary actuator 22 is provided on each of four sides of the block 19 to constitute a holding hand turning mechanism 21. The rotary actuator 22 has a blood sample conveying mechanism 24 with a holding hand 23.

Four holding hands 23 are protruded radially from the block 19. As shown in FIGS. 2A, 2B, 3A and 3B, each of the holding hands 23 includes a pair of arms 26 and an open/close mechanism 27 such as an air cylinder. The arms 26 have holding sections 25 for holding the sample container 1 at their distal ends. The open/close mechanism 27 opens and closes the holding sections 25 through the arms 26. The rotary actuator 22 and open/close mechanism 27 are driven upon receipt of a control signal from the controller 17. When the sample container 1 is located in the sensing position P2, the rotary actuator 22 tilts the sample container 1 held by the hand 23 by turning the holding hand 23 such that the cap 13 is directed downward.

The stroke of the main shaft 18 that is moved up and down by the driving mechanism 20 is set such that the sample container 1 held by the sample container holder 9 can be held and raised by the holding hand 23. The stroke is also set such that the sample container 1 held by the holding hand 23 can be inserted into the sample container holder 9. In the present embodiment, the intermittent-rotation angle of the blood sample conveying mechanism 24 is 90 degrees since the four holding hands 23 are arranged at 90-degree intervals. When the four holding hands 23 are located in the positions P1 to P4, the blood sample conveying mechanism 24 temporarily stops.

(Operation and Advantages of the Embodiment)

In order to conduct a test on whether the blood sample 3 contained in the sample container 1 is coagulated, the sample container is conveyed to the transfer position P1 through the conveyance path 2. When the sample container 1 reaches the position P1, the blood sample conveying mechanism 24 lowers.

While the mechanism 24 is lowering, the holding hand 23 is open, and the sample container 1 held by the sample container holder 9 is interposed between the paired holding sections 25. When the holding hand 23 is closed by the open/close mechanism 27, the middle of the sample container 1 is held by the holding sections 25. Thus, the driving mechanism 20 raises the mechanism 24. Accordingly, the sample container 1 is moved up in the vertical direction from the sample container holder 9.

When the driving mechanism 20 rotates the blood sample conveying mechanism 24 by 90 degrees in the direction of arrow A, the sample container 1 held by the holding hand 23 is located in the sensing position P2. If, then, the holding hand turning mechanism 21 is driven upon receipt of a control signal from the controller 17, the sample container 1 held by the holding hand 23 is tilted as illustrated in FIGS. 3B, 4A and 4B. In other words, the sample container 1 is tilted such that the cap 13 is directed downward.

When the sample container 1 is tilted, the light emitting element 15 of the optical sensing unit 14 emits test light L upon receipt of a control signal from the controller 17. If the blood sample 3 contained in the sample container 1 is not coagulated, it is fluid and thus collected in a downward direction or toward the cap 13 as shown in FIGS. 4A and 4B. If the blood sample 3 is coagulated, it is accumulated at the bottom of the sample container 1 as shown in FIG. 4C.

When the test light L enters the light-receiving element 16 through the sample container 1, the sensing unit 14 determines that the blood sample 3 is coagulated. When the test light L is shielded by the blood sample 3, the sensing unit 14 determines that the blood sample 3 is not coagulated. In accordance with each of the determinations, the light-receiving element 16 supplies a sensing signal to the controller 17.

When the test on whether the blood sample 3 is coagulated is completed, the driving mechanism 20 rotates the blood sample conveying mechanism 24 intermittently 90° by 90° in the direction of arrow A. When the sample container 1 whose blood sample 3 has been determined as being coagulated reaches the first separation position P3, the holding sections 25 of the holding hand 23 open and the sample container 1 drops into a first separation chute 28.

When the sample container 1 whose blood sample 3 is determined as not being coagulated passes the first separation position P3 and reaches the second separation position P4, the holding sections 25 of the holding hand 23 open and the sample container 1 drops into a second separation chute 29.

Consequently, the sample container 1 whose blood sample 3 is coagulated and the sample container 1 whose blood sample 3 is not coagulated are automatically separated from each other. When the holding hand 23 reaches the transfer position P1 on the conveyance path 2 again, the blood sample conveying mechanism 24 with the holding hand 23 lowers and repeats the same operations as described above.

According to the foregoing blood sample sensing apparatus, the sample container 1 containing a blood sample is automatically picked from the conveyance path 2 during the conveyance and then tilted and sensed by the optical sensing unit 14. It is thus possible to determine automatically and correctly whether the blood sample in the sample container 1 is coagulated, with the result that the efficiency of the operations can be improved and so can be the reliability of the test.

In the foregoing embodiment, the transfer position P1, sensing position P2, first separation position P3 and second separation position P4 are located at 90-degree intervals around the axis 0. This is one example of the present invention. These positions can be located linearly and the holding hands can be turned continuously. In the embodiment, the light-emitting and light-receiving elements 15 and 16, which serve as the optical sensing unit 14, are arranged opposite to each other. However, these elements can be arranged side by side to receive reflected light from a blood sample.

Though the optical sensing unit 14 senses the top portion of the sample container 1 which is tilted to be directed downward in the sensing position P2, the sensing unit 14 may sense the bottom portion of the sample container 1 which is tilted to be directed upward in the sensing position P2. In this case, it is determined that the blood sample 3 is coagulated when the test light L is shielded by the bottom portion of the sample container 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A blood sample sensing apparatus comprising:
   a moving device which moves a sample container containing a blood sample to a sensing position;
   a turning mechanism which is connected to the moving device and tilts the sample container such that a bottom of the sample container is directed upward when the sample container is located in the sensing position; and
   an optical sensor which is located in the sensing position and determines whether the blood sample in the sample container is coagulated,
   wherein the turning mechanism tilts the sample container such that an upper portion of the sample container is directed downward when the sample container is located in the sensing position, the bottom of the sample container being defined as a lower portion, and
   wherein the optical sensor senses whether the blood sample is accumulated in the upper portion of the sample container.

2. The blood sample sensing apparatus according to claim 1, further comprising a controller which determines that the blood sample is fluid when the optical sensor senses the blood sample and determines that the blood sample is coagulated when the optical sensor does not sense the blood sample.

3. The blood sample sensing apparatus according to claim 1, further comprising a conveyance path which holds the sample container and conveys the sample container to a position in which the sample container is moved to the moving device.

4. The blood sample sensing apparatus according to claim 1, wherein the sample container includes a tubular container and a cap fitted to a top opening of the tubular container.

5. The blood sensing apparatus according to claim 1, wherein the optical sensor includes:
   a light-emitting element which emits light to the sample container tilted by the turning mechanism; and
   a light-receiving element which receives light from the light-emitting element through the sample container, and
   the optical sensor outputs a first signal when the light-receiving element receives the light and a second signal when the light-receiving element does not receive the light.

6. The blood sample sensing apparatus according to claim 1, wherein the moving device further moves the sample container from the sensing position to a first separation section when the optical sensor determines that the blood sample is coagulated and to a second separation section when the optical sensor determines that the blood sample is not coagulated.

7. A blood sample sensing apparatus comprising:
   a moving device which moves a sample container containing a blood sample to a sensing position;
   a turning mechanism which is connected to the moving device and tilts the sample container such that a bottom of the sample container is directed upward when the sample container is located in the sensing position;
   an optical sensor which is located in the sensing position and determines whether the blood sample in the sample container is coagulated; and
   a conveyance path which holds the sample container and conveys the sample container to a position in which the sample container is moved to the moving device,
   wherein the moving device comprises moving units and a rotating member to which the moving units are connected and which moves each of the moving units from the conveyance path to the sensing position.

8. A blood sample sensing apparatus comprising:
   a moving device which moves a sample container containing a blood sample to a sensing position;
   a turning mechanism which is connected to the moving device and tilts the sample container such that a bottom of the sample container is directed upward when the sample container is located in the sensing position; and
   an optical sensor which is located in the sensing position and determines whether the blood sample in the sample container is coagulated,
   wherein the moving device includes a holding hand which holds and removes the sample container from a conveyance path.

9. A blood sample sensing apparatus comprising:
   a conveyance path which conveys a sample container which contains a blood sample and whose upper opening is closed with a cap, the sample container is being conveyed with the cap upward;
   a sensing device which is located in a midway point of the conveyance path and which senses a coagulation of the blood sample contained in the sample container;
   a driver which is provided in a position between the conveyance path and the sensing device and is freely rotated and moved up and down;
   blood sample conveying mechanisms provided in the driver and having holding hands, each of the holding hands holding the sample container that is being conveyed by the conveyance path when the driver moves down, raising the sample container from the conveyance path when the driver moves up, and conveying the sample container held by driving the driver to the sensing device; and
   a holding hand turning mechanism provided in each of the blood sample conveying mechanisms, which turns a corresponding holding hand to tilt the sample container such that the cap of the sample container held by the holding hand is directed downward when the holding hand is located near the sensing device.

10. The blood sample sensing apparatus according to claim 9, wherein the holding hands of the blood sample conveying mechanism are arranged radially around the driver and driven to process the sample container continuously.

11. The blood sample sensing apparatus according to claim 9, further comprising a separation section located downstream of the sensing device and which separates the sample container containing a coagulated blood sample and the sample container containing a blood sample not coagulated.

12. The blood sample sensing apparatus according to claim 9, wherein the sensing device includes a light-emitting element and a light-receiving element and determines that the blood sample is not coagulated when test light emitted from the light-emitting element is reflected or shielded by the blood sample in the sample container.

* * * * *